(12) United States Patent
Hindle et al.

(10) Patent No.: US 6,701,922 B2
(45) Date of Patent: Mar. 9, 2004

(54) MOUTHPIECE ENTRAINMENT AIRFLOW CONTROL FOR AEROSOL GENERATORS

(75) Inventors: Michael Hindle, Glen Allen, VA (US);
Peter R. Byron, Richmond, VA (US);
John N. Hong, Richmond, VA (US)

(73) Assignee: Chrysalis Technologies Incorporated, Richmond, VA (US)

( * ) Notice: Subject to any disclaimer, the term of this patent is extended or adjusted under 35 U.S.C. 154(b) by 0 days.

(21) Appl. No.: 10/022,739

(22) Filed: Dec. 20, 2001

(65) Prior Publication Data

US 2003/0136404 A1 Jul. 24, 2003

(51) Int. Cl.[7] .................... A61M 16/00; H05B 3/00
(52) U.S. Cl. ..................... 128/203.27; 128/203.12; 128/203.17; 128/203.26
(58) Field of Search ............. 128/203.12, 203.17, 128/203.26, 203.27, 203.28; 261/154, 130, 104, 177, DIG. 65

(56) References Cited

U.S. PATENT DOCUMENTS

| | | |
|---|---|---|
| 2,896,856 A | 7/1959 | Kravits |
| 3,084,698 A | 4/1963 | Smith |
| 3,157,179 A | 11/1964 | Paullus et al. |
| 3,162,324 A | 12/1964 | Houser |
| 3,431,393 A | 3/1969 | Katsuda |
| 3,486,663 A | 12/1969 | Humphrey |
| 3,658,059 A | 4/1972 | Steil |
| 3,716,416 A | 2/1973 | Adlhart et al. |
| 3,750,961 A | 8/1973 | Franz |
| 3,847,304 A | 11/1974 | Cohen |
| 3,859,398 A | 1/1975 | Havstad |
| 3,902,635 A | 9/1975 | Jinotti |
| 3,903,883 A | 9/1975 | Pecina et al. |
| 3,904,083 A | 9/1975 | Little |
| 3,967,001 A | 6/1976 | Almaula et al. |

(List continued on next page.)

FOREIGN PATENT DOCUMENTS

| | | |
|---|---|---|
| EP | 0358114 A | 3/1990 |
| EP | 0642802 A2 | 5/1996 |
| HU | 168128 B | 11/1977 |
| HU | 216121 B | 3/1991 |
| HU | P953409 | 6/1994 |
| WO | 94/09842 A | 5/1994 |
| WO | 98/17131 | 4/1998 |
| WO | WO99/39760 A | 8/1999 |

OTHER PUBLICATIONS

Notification of Transmittal of the International Search Report or the Declaration for PCT/US02/39900 dated May 20, 2003.

(List continued on next page.)

*Primary Examiner*—Weilun Lo
*Assistant Examiner*—Michael G. Mendoza
(74) *Attorney, Agent, or Firm*—Burns, Doane, Swecker & Mathis, LLP

(57) ABSTRACT

An aerosol generator includes a housing, a heater and a mouthpiece wherein the heater volatilizes liquid material within a flow passage and forms an aerosol in the mouthpiece. Mixing ambient air with the vaporized liquid material controls a droplet size of the aerosol. The ambient air can be directed into the mouthpiece by at least one air passageway in an airflow entrainment control member. The at least one air passageway provides a desired volume and/or velocity of ambient air entering into the mouthpiece thereby achieving a desired droplet size distribution of an aerosol. In an alternative arrangement, a funnel shaped airflow entrainment control member includes a narrow end proximate the outlet end of the flow passage. A cone angle of the funnel-shaped member can be selected to provide a desired volume of ambient air which mixes with the vaporized liquid material and achieves a desired aerosol droplet size distribution.

29 Claims, 2 Drawing Sheets

U.S. PATENT DOCUMENTS

| | | |
|---|---|---|
| 3,987,941 A | 10/1976 | Blessing |
| 3,993,246 A | 11/1976 | Erb et al. |
| 3,995,371 A | 12/1976 | O'Keefe |
| 4,042,153 A | 8/1977 | Callahan et al. |
| 4,060,082 A | 11/1977 | Lindberg et al. |
| 4,077,542 A | 3/1978 | Petterson |
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,259,409 A | 3/1981 | Arnold |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |
| 4,395,303 A | 7/1983 | Weir |
| 4,433,797 A | 2/1984 | Galia |
| 4,471,892 A | 9/1984 | Coleman |
| 4,512,341 A | 4/1985 | Lester |
| 4,575,609 A | 3/1986 | Fassel et al. |
| 4,604,999 A * | 8/1986 | Maeda .................. 128/200.21 |
| 4,627,432 A | 12/1986 | Newell et al. |
| 4,649,911 A | 3/1987 | Knight et al. |
| 4,682,010 A | 7/1987 | Drapeau et al. |
| 4,695,625 A | 9/1987 | Macdonald |
| 4,700,657 A | 10/1987 | Butland |
| 4,730,111 A | 3/1988 | Vestal et al. |
| 4,735,217 A | 4/1988 | Gerth et al. |
| 4,744,932 A | 5/1988 | Browne |
| 4,749,778 A | 6/1988 | Fukuzawa et al. |
| 4,762,995 A | 8/1988 | Browner et al. |
| 4,776,515 A | 10/1988 | Michalchik |
| 4,790,305 A | 12/1988 | Zoltan et al. |
| 4,811,731 A | 3/1989 | Newell et al. |
| 4,819,625 A | 4/1989 | Howe |
| 4,819,834 A | 4/1989 | Thiel |
| 4,829,996 A | 5/1989 | Noakes et al. |
| 4,837,260 A | 6/1989 | Sato et al. |
| 4,848,374 A | 7/1989 | Chard et al. |
| 4,871,115 A | 10/1989 | Hessey |
| 4,871,623 A | 10/1989 | Hoopman et al. |
| 4,877,989 A | 10/1989 | Drews et al. |
| 4,911,157 A | 3/1990 | Miller |
| 4,922,901 A | 5/1990 | Brooks et al. |
| 4,926,852 A | 5/1990 | Zoltan et al. |
| 4,935,624 A | 6/1990 | Henion et al. |
| 4,941,483 A | 7/1990 | Ridings et al. |
| 4,942,874 A * | 7/1990 | Terada et al. .......... 128/203.16 |
| 4,947,875 A | 8/1990 | Brooks et al. |
| 4,974,754 A | 12/1990 | Wirz |
| 4,982,097 A | 1/1991 | Slivon et al. |
| 4,992,206 A | 2/1991 | Waldron |
| 5,021,802 A | 6/1991 | Allred |
| 5,044,565 A | 9/1991 | Alexander |
| 5,056,511 A | 10/1991 | Ronge |
| 5,060,671 A | 10/1991 | Counts et al. |
| 5,063,921 A | 11/1991 | Howe |
| 5,086,766 A * | 2/1992 | Beacham ............... 128/203.27 |
| 5,096,092 A | 3/1992 | Devine |
| 5,125,441 A | 6/1992 | Mette |
| 5,133,343 A | 7/1992 | Johnson, IV et al. |
| 5,134,993 A | 8/1992 | van der Linden et al. |
| 5,135,009 A | 8/1992 | Müller et al. |
| 5,144,962 A | 9/1992 | Counts et al. |
| 5,151,827 A | 9/1992 | Ven et al. |
| 5,178,305 A | 1/1993 | Keller |
| 5,184,776 A | 2/1993 | Minier |
| 5,217,004 A | 6/1993 | Blasnik et al. |
| 5,226,441 A | 7/1993 | Dunmire et al. |
| 5,228,444 A | 7/1993 | Burch |
| 5,230,445 A | 7/1993 | Rusnak |
| 5,231,983 A | 8/1993 | Matson et al. |
| 5,259,370 A | 11/1993 | Howe |
| 5,290,540 A | 3/1994 | Prince et al. |
| 5,298,744 A | 3/1994 | Mimura et al. |
| 5,299,565 A | 4/1994 | Brown |
| 5,322,057 A | 6/1994 | Raabe et al. |
| 5,327,915 A | 7/1994 | Porenski et al. |
| 5,342,180 A | 8/1994 | Daoud |
| 5,342,645 A | 8/1994 | Eisele et al. |
| 5,349,946 A | 9/1994 | McComb |
| 5,395,445 A | 3/1995 | Bohanan |
| 5,421,489 A | 6/1995 | Holzner, Sr. et al. |
| 5,462,597 A | 10/1995 | Jubran |
| 5,474,059 A | 12/1995 | Cooper |
| 5,509,557 A | 4/1996 | Jimarez et al. |
| 5,515,842 A | 5/1996 | Ramseyer et al. |
| 5,522,385 A | 6/1996 | Lloyd et al. |
| 5,556,964 A | 9/1996 | Hofstraat et al. |
| 5,564,442 A | 10/1996 | MacDonald et al. |
| 5,565,677 A | 10/1996 | Wexler et al. |
| 5,568,807 A * | 10/1996 | Mecikalski ............ 128/203.21 |
| 5,575,929 A | 11/1996 | Yu et al. |
| 5,585,045 A | 12/1996 | Heinonen et al. |
| 5,617,844 A | 4/1997 | King |
| 5,642,728 A | 7/1997 | Andersson et al. |
| 5,674,860 A | 10/1997 | Carling et al. |
| 5,682,874 A | 11/1997 | Grabenkort et al. |
| 5,730,158 A | 3/1998 | Collins et al. |
| 5,743,251 A | 4/1998 | Howell et al. |
| 5,756,995 A | 5/1998 | Maswadeh et al. |
| 5,765,724 A | 6/1998 | Amberg et al. |
| 5,823,178 A | 10/1998 | Lloyd et al. |
| 5,839,430 A | 11/1998 | Cama |
| 5,855,202 A | 1/1999 | Andrade |
| 5,856,671 A | 1/1999 | Henion et al. |
| 5,863,652 A | 1/1999 | Matsumura et al. |
| 5,869,133 A | 2/1999 | Anthony et al. |
| 5,872,010 A | 2/1999 | Karger et al. |
| 5,878,752 A | 3/1999 | Adams et al. |
| 5,881,714 A | 3/1999 | Yokoi et al. |
| 5,894,841 A * | 4/1999 | Voges .................... 128/203.12 |
| 5,906,202 A | 5/1999 | Schuster et al. |
| 5,914,122 A | 6/1999 | Otterbeck et al. |
| 5,932,249 A | 8/1999 | Gruber et al. |
| 5,932,315 A | 8/1999 | Lum et al. |
| 5,934,272 A | 8/1999 | Lloyd et al. |
| 5,934,273 A | 8/1999 | Andersson et al. |
| 5,944,025 A | 8/1999 | Cook et al. |
| 5,954,047 A * | 9/1999 | Armer et al. .......... 128/200.23 |
| 5,954,979 A | 9/1999 | Counts et al. |
| 5,957,124 A | 9/1999 | Lloyd et al. |
| 5,970,973 A | 10/1999 | Gonda et al. |
| 5,970,974 A | 10/1999 | Van Der Linden et al. |
| 5,978,548 A | 11/1999 | Holmstrand et al. |
| 5,993,633 A | 11/1999 | Smith et al. |
| 6,014,970 A | 1/2000 | Ivri et al. |
| 6,053,176 A | 4/2000 | Adams et al. |
| 6,054,032 A | 4/2000 | Haddad et al. |
| 6,069,214 A | 5/2000 | McCormick et al. |
| 6,069,219 A | 5/2000 | McCormick et al. |
| 6,070,575 A | 6/2000 | Gonda et al. |
| 6,071,428 A | 6/2000 | Franks et al. |
| 6,071,554 A | 6/2000 | Isomura et al. |
| 6,076,522 A | 6/2000 | Dwivedi et al. |
| 6,077,543 A | 6/2000 | Gordon et al. |
| 6,080,721 A | 6/2000 | Patton |
| 6,085,740 A | 7/2000 | Ivri et al. |

| | | |
|---|---|---|
| 6,085,753 A | 7/2000 | Gonda et al. |
| 6,089,228 A | 7/2000 | Smith et al. |
| 6,095,141 A * | 8/2000 | Armer et al. .......... 128/204.26 |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,155,268 A | 12/2000 | Takeuchi |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Ganan-Calvo |
| 6,187,344 B1 | 2/2001 | Eljamal et al. |
| 6,189,803 B1 | 2/2001 | Gañán-Calvo |
| 6,192,882 B1 | 2/2001 | Gonda |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 6,341,605 B1 * | 1/2002 | Ohki et al. ............ 128/203.15 |
| 6,347,629 B1 * | 2/2002 | Braithwaite ............ 128/203.15 |
| 6,367,472 B1 * | 4/2002 | Koch .................... 128/203.12 |
| 2001/0032647 A1 | 10/2001 | Schuster et al. |

OTHER PUBLICATIONS

Barry, P.W. et al. "In Vitro Comparison of the Amount of Salbutamol Available for Inhalation From Different Formulations Used with Different Spacer Devices" Eur Respir J 1997; 10: 1345–1348.

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994.

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp. 97–102.

Hou, Shuguang et al. *Solution Stability of Budensonide in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766–770, Jul. 1980.

* cited by examiner

MOUTHPIECE ENTRAINMENT AIRFLOW CONTROL FOR AEROSOL GENERATORS

BACKGROUND OF THE INVENTION

1. Field of the Invention

The present invention relates generally to aerosol generation. More specifically, the present invention relates to the use of mouthpiece entrainment airflow members for controlling aerosol size distributions from an aerosol generator.

2. Description of Related Art

Aerosols are useful in a wide variety of applications. For example, it is often desirable to treat respiratory ailments with, or deliver medicaments by means of, aerosol sprays of finely divided particles of liquid and/or solid, such as powders, liquid medicaments, and the like, which are inhaled into a patient's lungs. Aerosols are also used for such purposes as providing desired scents to rooms, applying scents to the skin, and delivering paint and lubricant.

Various techniques are known for generating aerosols, particularly in the field of medicine. For example, U.S. Pat. Nos. 4,811,731 and 4,627,432 both disclose devices for administrating medicaments to patients in which a capsule is pierced by a pin to release medicament in powder form. The user inhales released medicament through an opening in the device. Medicaments in liquid form are known to be delivered by generation of an aerosol with a manually operated pump. The pump draws liquid from a reservoir and forces it through a small nozzle opening to form a fine spray.

Both of these methods of generating an aerosol for the delivery of medicaments suffer from problems. The aerosols produced by these techniques contain substantial quantities of particles or droplets which are too large to be inhaled. Persons who have difficulty in generating a sufficient flow of air through the device to properly inhale the medicaments, such as asthma or emphysema sufferers, have particular difficulty in using these devices.

An alternate means of delivering a medicament is generating an aerosol including liquid or powder particles by means of a compressed propellant, usually a chloro-fluorocarbon (CFC) or hydrofluous alkane (HFA), which entrains the medicament, usually by the Venturi principle. Such inhalers are usually operated by depressing a button to release a short charge of the compressed propellant which contains the medicament through a spray nozzle, allowing the propellant encapsulated medicament to be inhaled by the user. However, it is difficult to properly synchronize the inhalation of the medicament with depression of the actuator. Further, large quantities of medicament or other materials are not suitably delivered by this method. This method is better suited to delivery of such materials as antiperspirants, deodorants and paints.

Many aerosol generators also are unable to generate aerosols having an average mass median aerosol diameter (MMAD) less than 2 to 4 microns, and are incapable of delivering high aerosol mass flow rates, such as above 1 milligram per second, with particles in the range of 0.2 to 2.0 microns. A high aerosol mass flow rate and small particle size are particularly desirable for better penetration of the lungs during medicament administration, such as for asthma treatment.

Large particles generated by metered dose inhalers may be deposited in the mouth and pharynx of the patient, rather than inhaled into the lungs. Further, what is inhaled may not penetrate the lungs deeply enough. Therefore, it is known to add a spacer chamber to a pressurized inhaler mechanism in order to allow the propellant time to evaporate, decreasing the mass median aerosol diameter of the particles. See, for example, U.S. Pat. No. 5,855,202 to Andrade and *Eur. Respir. J.* 1997; 10:1345–1348. Particles from metered dose inhalers may have an MMAD of 5–6 $\mu$m. The use of a spacer chamber in such a case reduces the particle MMAD to about 1.5 $\mu$m or greater, enhancing medicament deposition in the lung as opposed to the mouth or throat. See, for example, *Eur. Respir. J.* 1997, 10:1345–1348; *International Journal of Pharmaceutics*, 1 (1978) 205–212 and *Am. Rev. Respir. Dis.* 1981, 124:317–320.

Spacer chambers also are known to affect the output of the aerosol device because of the static charge which may be created therein. Medicament particles may be deposited in spacer chambers by electrostatic attraction to the spacer chamber wall, by inertial impaction, or by gravitational settling over time. Further, different medicaments behave differently within such spacer chambers based on particle size, particle charge, and the like. Thus, loss of medicament occurs within spacer chambers and is a drawback to effective spacer chamber use. See *Eur. Respir. J.* 1997; 10:1345–1348.

Therefore a need exists for a device which provides differing aerosol size distributions of an aerosol produced by an aerosol generator depending on the needs of a patient. Moreover, this device should allow adjustment of a aerosol size distribution of an aerosol produced by an aerosol generator.

BRIEF SUMMARY OF THE INVENTION

The present invention fills the aforementioned needs by providing an aerosol generator having an airflow entrainment control member which allows for control of the aerosol size distribution of an aerosol exiting the aerosol generator. The airflow entrainment control member may be adapted for different aerosol size distributions depending on the needs of the user.

In one embodiment of the present invention, an aerosol generator includes a housing, a heater, a mouthpiece, a source of liquid material to be volatilized and an airflow entrainment control member. The housing includes a flow passage disposed therein which allows for heating of material from the source of material as the material passes into the flow passage. The heater is disposed along the flow passage and heats the flow passage, thereby volatilizing the material within the flow passage. The mouthpiece is located proximate an outlet end of the flow passage such that upon volatilization of the material within the heated passage, the volatilized material passes into the condensation region of the mouthpiece. The airflow entrainment control member is also disposed about the outlet end of the flow passage within the mouthpiece. The airflow entrainment control member is configured to control volume and/or velocity of air passing into the mouthpiece such that the air admixes with the volatilized material and forms an aerosol. Since the airflow entrainment control member controls volume and/or velocity of air passing into the mouthpiece, the airflow entrainment control member may be used to control the aerosol size distribution delivered by the aerosol generator.

In another embodiment of the present invention, a method for generating a volatilized material using the aerosol generator described above includes supplying liquid material to a flow passage contained within a housing of the aerosol generator, heating of the liquid material in the flow passage and directing the volatilized liquid material out of the flow passage and into the mouthpiece for admixing with external air passing through an airflow entrainment control member disposed proximate the outlet of the flow passage. The airflow entrainment control member is configured to control the volume and/or velocity of the external air passing into the mouthpiece, thereby controlling the aerosol size distribution of an aerosol delivered by the aerosol generator. In this embodiment, the airflow entrainment control member includes one or more airflow passages disposed therein. When the airflow entrainment control member is provided with a constant volumetric airflow rate, the size and number of the air passageways alters and controls the velocity of the available entrainment air in a condensation region of the aerosol generator. In this embodiment, the volumetric airflow rate of air into the airflow entrainment control member may also alter and control the velocity of the available entrainment air in the condensation region of the aerosol generator.

In a further embodiment of the present invention, a method for manufacturing the aerosol generator described above includes attaching the airflow entrainment control member to the aerosol generator housing at the downstream end of the flow passage.

In yet another embodiment of the present invention, an airflow entrainment control member in accordance with the present invention, may include a cone configuration disposed at a given angle. In this embodiment, a constant volumetric air flow rate is supplied to the cone where the angle of the cone determines the volume of entrainment air available. Therefore, the cone angle alters and controls the volume of entrainment air available in the condensation region. In this embodiment, the volumetric airflow rate of air supplied to the cone may also be altered. The ratio of available entrainment air in the condensation region will be controlled by the cone angle, thus controlling aerosol particle size.

BRIEF DESCRIPTION OF THE SEVERAL VIEWS OF THE DRAWING(S)

Various advantages of the present invention will be apparent to those skilled in the art with a reading of this specification in conjunction with the attached drawings, wherein like reference numerals are applied to like elements and wherein.

DETAILED DESCRIPTION OF THE INVENTION

The present invention provides an aerosol generator having an airflow entrainment control member. As an overview, an aerosol generator in accordance with the present invention includes an airflow entrainment control member which controls a droplet size distribution of an aerosol produced by the aerosol generator. In one embodiment of the present invention, the airflow entrainment control member has a circular configuration having passageways radially disposed from a center of the airflow entrainment control member. The passageways control a droplet size distribution of the aerosol produced by the aerosol generator. In accordance with another embodiment of the present invention, an aerosol generator includes a replaceable airflow entrainment control member which permits a user to change the airflow entrainment control member to provide a different droplet size distribution.

Figure 1:
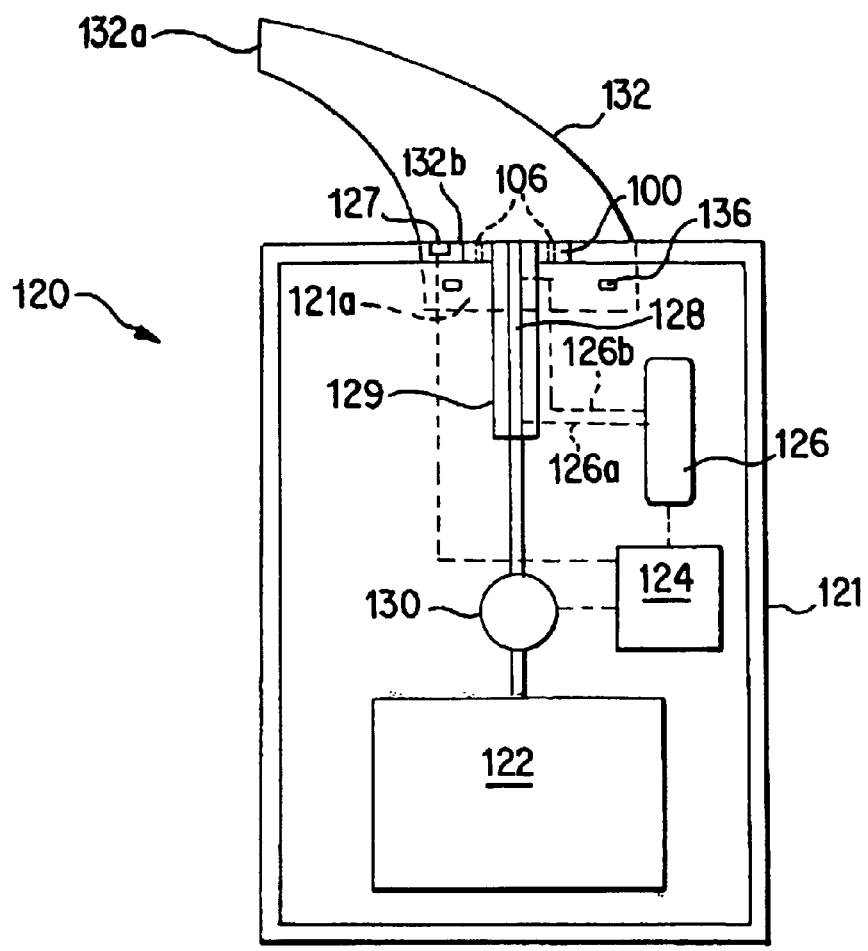
FIG. 1 is a schematic of an aerosol generator in accordance with one embodiment of the present invention.

FIG. 1 is a schematic of a hand-held aerosol generator 120 in accordance with one embodiment of the present invention. The aerosol generator 120 comprises a housing 121 which includes a source 122 of liquid material, a controller 124, a power source 126, an optional sensor 127 such as a pressure sensor, a heated flow passage 128, a valve 130 and a mouthpiece 132. The source 122 may be a medicament or drug formulation, such as a solution containing a medicated material, for delivery to a patient. The valve 130 or other suitable arrangement such as a syringe pump can be operated to deliver a predetermined volume of fluid from the source 122 to the flow passage 128. As will be discussed in greater detail further on, the aerosol generator may be configured for delivery of material supplied by the source 122 within various regions of a patient's lung, such as the central lung portion or the deep lung portion. The controller 124 is operably connected to the power source 126, the sensor 127 and the valve 130 to effect delivery of liquid material to the flow passage 128 and operate a heater associated with the flow passage 128 (e.g., the flow passage can comprise a metal tube which is resistively heated or a passage in a body which includes a resistance heater arranged to heat the fluid passing through the flow passage).

According to one aspect of the present invention, the heated flow passage 128 comprises a stainless steel tube or other electrically conductive material, or a non-conductive or semi-conductive tube incorporating a heater formed from an electrically conductive material such as platinum (Pt). The flow passage is preferably a capillary sized passage of uniform cross-section along the length thereof, having a diameter preferably between about 0.1 to 10 mm, more preferably 0.1 to 1 mm, and most preferably 0.15 to 0.5 mm. However, the capillary passage can have other configurations defined by a transverse cross sectional area from about $8 \times 10^{-5}$ mm$^2$ to about 80 mm$^2$, preferably about $2 \times 10^{-3}$ mm$^2$ to about $8 \times 10^{-1}$ mm$^2$, and more preferably about $8 \times 10^{-3}$ mm$^2$ to about $2 \times 10^{-1}$ mm$^2$.

The flow passage 128 may be formed so as to extend in a linear or non-linear direction. As may be seen with reference to FIG. 1, the flow passage 128 includes a section within body 129 (e.g., the flow passage 128 can comprise a section of tubing supported coaxially within a glass tube of larger dimensions sealed at opposed ends thereof to provide an air space between the outer surface of the metal tube and the inner wall of the glass tube). The section of the flow passage 128 within the body 129 can be heated by passing electrical current through a heater comprising a resistive heating material (e.g., a section of metal tubing forming the flow passage or a separate heater located along the flow passage). For example, direct current can be passed through the resistive heating material via electrical lines 126a, 126b attached to positive and negative electrodes of battery 126.

With the arrangement shown in FIG. 1, when the controller 124 activates the power supply to pass the electrical current through the heater formed by the resistive heating material, the liquid material in the flow passage 128 is vaporized. In an embodiment of the present invention, the hand-held aerosol generator 120 includes a power supply such as the previously mentioned battery which supplies direct current to the heater formed by a portion of a stainless steel tube between electrical contacts (not shown) on the tube to which lines 126a and 126b are attached. However, in the case where the aerosol generator is a laboratory or industrial unit, the power can be supplied by an external power source rather than a battery housed within the aerosol generator. As the power supply supplies electric current, the electric current resistively heats the heater material, thereby causing volatilization of the liquid material within the flow passage 128. For example, the controller 124 can be programmed to activate the power supply in an intermittent manner so as to heat the flow passage 128 for a predetermined time interval while a predetermined volume of fluid is supplied to the flow passage 128.

Other arrangements which can be used to effect volatilization of the liquid material within the flow passage 128 include a laminate body having opposed layers bonded together, where a flow passage is disposed between the layers, as described in commonly owned U.S. application Ser. No. 09/742,320 filed Dec. 22, 2000, the disclosure of which is hereby incorporated by reference. Another arrangement which can be used is an inductive heating arrangement as disclosed in commonly owned U.S. application Ser. No. 09/742,323 filed on Dec. 22, 2000, the disclosure of which is hereby incorporated by reference. In an embodiment using an inductive heating arrangement, a current is passed through one or more inductive heating coils which produces an electromagnetic flux in an electrically conductive heating element located such that the flux produces eddy currents inside the heating element which in turn heats the heating element. This heat is then transferred to the liquid material within the flow passage 128 either by direct or indirect thermal conduction. Another heating arrangement which can be used is a resistance heater such as a thin platinum layer located along the flow passage, as fully described in U.S. Pat. Nos. 5,743,251 and 6,234,167, the disclosures of which are hereby incorporated by reference.

In a preferred embodiment of an inhaler according to the present invention, the mouthpiece 132 has a volumetric capacity in a range between about 5 cc and about 10 cc. The mouthpiece 132 includes a mouthpiece opening 132a through which the aerosol generated by the aerosol generator 120 exits to a patient inhaling the aerosol. In order to supply air for mixing with the volatilized liquid material, the aerosol generator 120 can include vent holes 136 disposed within an outer wall of the housing 121 enclosing the airflow entrainment control member 100 such that the vent holes 136 allow for the passage of external air into the aerosol generator 120. The external air passes into a chamber 121a within the aerosol generator 120 via the vent holes 136 and then through one or more passageways 106 of the airflow entrainment control member 100. However, the vent holes 136 can be omitted and the air entrainment control member can be arranged such that external air passes directly through the one or more passageways 106. Upon passage through the one or more passageways 106, the external air enters the mouthpiece 132 for admixture with the volatilized liquid material exiting the heated flow passage 128 into a condensation region within the mouthpiece 132. The mouthpiece opening 132a is separated from the outlet end of the heated flow passage 128 by a space 132b. As such, air passing through the airflow entrainment control member 100 and into the space 132b admixes with the volatilized liquid material prior to exiting through the mouthpiece opening 132a. It should be noted that in addition to external air, other gases (e.g., nitrogen) suitable for dilution of medicament within the hand held aerosol generator may pass through the passageways 106 for mixing with the volatilized fluid exiting the heated flow passage 128.

During operation of the aerosol generator 120, the valve 130 may be opened to allow a desired volume of liquid material from the source 122 to enter the flow passage 128. The valve 130 may be opened either prior to or subsequent to detection by the sensor 127 of vacuum pressure applied to the mouthpiece 132 by a user attempting to inhale aerosol from the aerosol generator 120. While liquid material passes through the flow passage 128, the liquid material heats to a suitable temperature for volatilizing the liquid material. Liquid material from the source 122 can be fed into the flow passage 128 at a substantially constant pressure and/or in a predetermined volume. The volatilized liquid material exits the flow passage 128 through an outlet end of the flow passage 128 and forms an aerosol which can be inhaled by a user drawing upon the mouthpiece 132.

The airflow entrainment control member 100 may be employed to control the volume and/or the velocity of entrainment air entering the mouthpiece 132. As more clearly shown with reference to FIG. 3, in one embodiment of the present invention, the airflow entrainment control member 100 has a circular configuration with a plurality of passageways 106 disposed about a central opening 104 of the airflow entrainment control member 100. At a constant flow rate of air into the mouthpiece, the airflow entrainment control member 100 can provide a desired aerosol size distribution and/or flow rate of aerosol droplets out of the mouthpiece 132. Thus, by controlling the volume and/or velocity of air passing into the mouthpiece 132 and admixing with the vaporized liquid material of defined mass, the airflow entrainment control member 100 can control an aerosol size distribution or mass median aerodynamic diameter of the aerosol droplets delivered to a patient.

In one embodiment of the present invention, the number and/or size of the one or more passageways 106 can be selected to achieve a desired volume and/or velocity of air passing into the mouthpiece 132 and thus control the aerosol droplet size. According to a preferred embodiment, the one or more passageways 106 can comprise a circumferential row of spaced apart holes located at least 10 mm from the central axis of the flow passage 128. For instance, 10 evenly spaced holes having diameters of 1.5 to 3 mm can be located 10 mm or 15 mm from the central axis. In general, it has been found that for a constant volumetric airflow, increasing the airflow velocity in the condensation region by decreasing either the size or number or both of airflow passageways in the airflow entrainment control member 100 provides decreased aerosol droplet size.

For deep lung penetration, the passageways 106 may be configured to achieve an airflow rate and/or airflow velocity which provides droplets having a mass median aerodynamic diameter in a range between about 0.2 microns to about 0.5 microns. In addition, if the requirements of a user necessitate central lung deposition, the passageways 106 may be configured to provide droplets having a mass median aerodynamic diameter in a range between about 1 micron and about 2 microns. It is to be understood that the passageways 106 may be configured for deposition of a medicament within any area of the lung in addition to central lung and deep lung deposition.

In the examples shown with reference to Table I, a 28 gauge (28 Ga) and a 32 gauge (32 Ga) flow passage having a length of 44 mm was used. Likewise, the medicament was delivered to the flow passage at rates of 2.5 mg/sec. and 5.0 mg/sec. Moreover, the resultant aerosol droplets formed had 0.5% and 0.1% budesonide (Bud) in the entrainment vehicle (propylene glycol). The data shown with respect to the table indicates the mass median aerodynamic diameter of the vehicle (propylene glycol(PG)) and the medicament (Bud).

TABLE I

Effect of Air Entrainment Control Member on the MMAD of budesonide in PG Aerosols

| | | | | | | | |
|---|---|---|---|---|---|---|---|
| Flow Passage Diameter | 32Ga | 32Ga | 28Ga | 28Ga | 28Ga | 28Ga | 28Ga |
| Length of Flow Passage | 44 mm | 44 mm | 44 mm | 44 mm | 44 mm | 44 mm | 44 mm |
| Percentage of Bud in PG | 0.5% | 0.5% | 0.5% | 0.5% | 0.1% | 0.1% | 0.1% |
| Medicament Flow Rate | 2.5 mg/sec | 2.5 mg/sec | 5.0 mg/sec | 5.0 mg/sec | 5.0 mg/sec | 5.0 mg/sec | 5.0 mg/sec |
| Delivery Adapter | No | Yes | No | Yes | No | Yes | Yes |
| # of Holes | | 10 | | 10 | | 10 | 10 |
| Diameter of Holes | | 1.5 mm | | 1.5 mm | | 1.5 mm | 3.0 mm |
| Radial Distance | | 10 mm | | 10 mm | | 10 mm | 10 mm |
| MMAD of PG | 0.46 μm | 0.70 μm | 0.50 μm | 0.77 μm | 0.70 μm | 0.85 μm | 0.92 μm |
| MMAD of Bud | | | 0.36 μm | 0.40 μm | 0.54 μm | 0.56 μm | 0.71 μm |

It should be noted that the aerosol size distribution may be further controlled through additional parameters, including, but not limited to, controlling an amount of air passing through the airflow entrainment control member 100. Likewise, aerosol size distribution may be further controlled by controlling the temperature of air passing through the airflow entrainment control member and controlling a ratio of an amount of vapor mass to an amount of dilution air. Dilution air entering the airflow entrainment control member 100 may be added by physical entrainment or by controlling an inhalation rate by a user of the hand-held aerosol generator 120. In an embodiment using physical entrainment, a supplemental source of gas, such as a compressed air source physically located within the hand held aerosol generator 120 (not shown) provides dilution air to the airflow entrainment control member 100 and/or directly to the interior of the mouthpiece. As such, by controlling volume and/or velocity from the supplemental source of air, the aerosol size distribution of an aerosol may be controlled. In addition, the user may control a rate of inhalation while using the hand held aerosol generator 120, thereby controlling the amount of ambient air entering the airflow entrainment control member 100 and controlling aerosol size distribution.

In addition to controlling the amount of air entering the airflow entrainment control member, both the temperature of the air and the amount of vapor mass delivered by the flow passage 128 to the condensation regions 132 may be controlled. By controlling the temperature of the air entering the airflow entrainment control member 100, the aerosol size distribution may be controlled. In addition, the amount of vapor mass delivered by the flow passage controls the aerosol size distribution. By varying the amount of delivered vapor mass, the ratio of the vapor mass to an amount of dilution air may be controlled thereby controlling the aerosol size distribution delivered to the user.

In an embodiment of the present invention, the airflow entrainment control member 100 can be removably attached to the aerosol generator by any suitable arrangement (e.g., threaded connection, snap fit connection, etc.) so that it may be interchanged with a second airflow entrainment control member (not shown) which allows for a different volume and/or velocity of air passing into the mouthpiece 132. Therefore, the aerosol generator 120 may be adaptable for a variety of lung depositions within a user. Such interchangeability is also useful in a laboratory aerosol generator used to study aerosol formation or in a commercial apparatus wherein a predetermined aerosol size may be desired. To further illustrate, if a user having the aerosol generator 120 configured for deep lung penetration as described earlier desires to use the aerosol generator 120 for central lung deposition, the airflow entrainment control member configured for deep lung penetration can be replaced with an airflow entrainment control member configured for central lung deposition. Alternatively, the airflow entrainment control member can be designed such that volume and/or velocity of air into the mouthpiece is adjustable (e.g., a rotatable disk or other arrangement can be used to change the size of the passageways 106 and thus control the flow rate of air into the mouthpiece).

Figure 3:
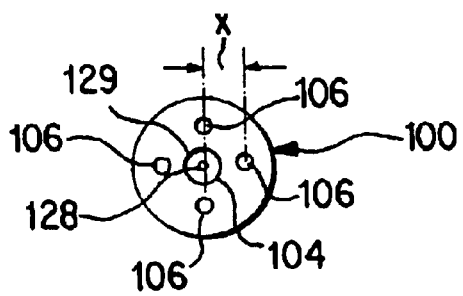
FIG. 3 shows an end view of an airflow entrainment control member of the aerosol generator shown with reference to FIG. 1.

As may be seen more clearly with respect to FIG. 3, the outlet end of the flow passage 128 is located adjacent the central opening 104 of the airflow entrainment control member 100. If desired, the outlet end can be arranged so as to protrude into the mouthpiece 132 of the aerosol generator 120. In either case, ambient air traveling through the airflow entrainment control member 100 mixes with volatilized liquid material passing through the flow passage 128 in a space within the mouthpiece 132. However, it should be noted that in an alternative embodiment of the present invention, the airflow entrainment control member can itself be a mouthpiece. In this embodiment, admixing of vaporized liquid material passing through the flow passage 128 and air passing through the airflow entrainment control member 100 would be admixed within the mouth of a user.

Figure 2:
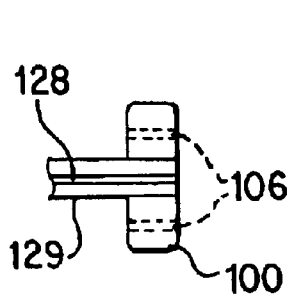
FIG. 2 is a side view of an airflow entrainment control member of the aerosol generator shown with reference to FIG. 1.
Figure 4:
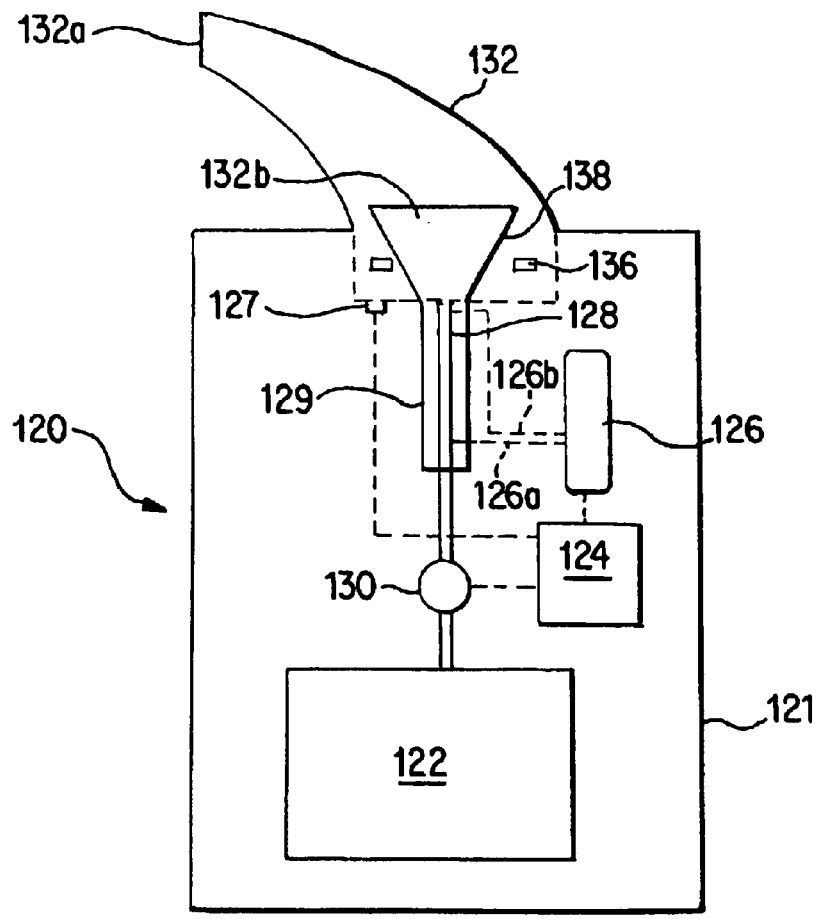
FIG. 4 illustrates a schematic of an alternative embodiment of an aerosol generator.
Figure 5:
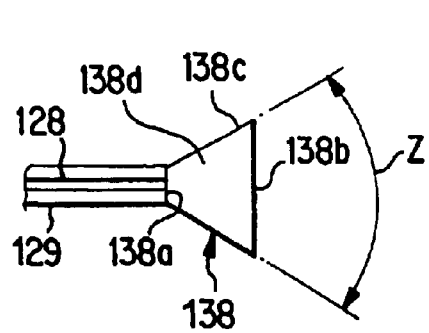
FIG. 5 shows a side view of an airflow entrainment control member of the aerosol generator shown with reference to FIG. 4.
Figure 6:
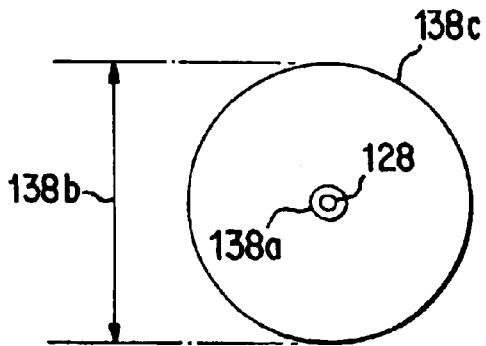
FIG. 6 shows an end view of an airflow entrainment control member of the aerosol generator shown with reference to FIG. 4.

In addition to the airflow entrainment control member 100 shown with reference to FIGS. 1 through 3, an airflow entrainment control member 138 in accordance with an alternative embodiment of the present invention may have the configuration shown with respect to FIG. 4. In this embodiment, the airflow entrainment control member 138 includes a funnel-shaped or conical configuration having a narrow end 138a and a wide end 138b. The ends 138a and 138b define a cone angle Z which is the angle formed within the outer side wall 138c of the member 138, as shown with reference to FIG. 5. The cone angle Z controls the volume of volatilized liquid material passing into the condensation space 138d from the flow passage 128 into the mouthpiece 132. As such, the cone angle Z controls the aerosol size distribution of aerosol delivered to a user. In this embodiment, aerosol size increases as the cone angle and the corresponding volume of the cone defined by ends 138a and 138b decreases due to alterations in vapor nucleation and droplet coagulation rates. As an example, the member 138 can have a length of about 6 cm and the central opening at the narrow end 138a can be about 1.2 cm so as to be fitted around body 129. The cone angle can be any desired angle (e.g., 10 to 100°). In tests, the following results were achieved using a 28 gauge stainless steel tube as the flow passage with a heated length of 44 mm while supplying 0.8 wt % Benzil (BZ) in propylene glycol (PG) to the flow passage at a rate of 5 mg/second for 3 seconds (Table II).

TABLE II

Effect of Airflow Entrainment Control Member on the MMAD of Benzil in PG Aerosols

| Cone Angle (°) | MMAD ($\mu$m) PG | MMAD ($\mu$m) BZ |
|---|---|---|
| 29 | 1.11 | 1.08 |
| 34 | 1.08 | 1.04 |
| 42 | 0.99 | 0.98 |
| 50 | 0.78 | 0.76 |
| 70 | 0.77 | 0.76 |
| 82 | 0.77 | 0.76 |

In a further example, the following results set forth in Table II were achieved using a 28 gauge stainless steel tube as the flow passage with a heated length of 44 mm. A supply of 0.37% Benzil in propylene glycol (PG) was provided to the flow passage at a rate of 5 mg/sec for 5 seconds.

TABLE III

Effect of Airflow Entrainment Control Member on the MMAD of Benzil in PG Aerosols

| Cone Angle (°) | MMAD ($\mu$m) PG | MMAD ($\mu$m) BZ |
|---|---|---|
| 24 | 1.21 | 1.15 |
| 30 | 1.05 | 1.01 |
| 37 | 0.89 | 0.84 |
| 43 | 0.78 | 0.74 |
| 51 | 0.66 | 0.64 |
| 61 | 0.62 | 0.59 |
| 78 | 0.60 | 0.57 |

The above are exemplary modes of carrying out the invention and are not intended to be limiting. It will be apparent to those of ordinary skill in the art that modifications thereto can be made without departure from the spirit and scope of the invention as set forth in the accompanying claims.

What is claimed is:

1. An aerosol generator, comprising:

a housing having a flow passage therein;

a heater arranged along the flow passage and operable to vaporize liquid material passing through the flow passage;

a mouthpiece having an interior thereof in fluid communication with an outlet end of the flow passage;

a source of liquid material to be volatilized, the source of liquid material being in fluid communication with an inlet of the flow passage; and at least one air passageway disposed within an airflow entrainment control member which is disposed at the outlet end of the flow passage, the at least one air passageway admits air from outside the mouthpiece to the interior of the mouthpiece, the at least one air passageway being operable to deliver a predetermined volume and/or velocity of air into the mouthpiece which mixes with the volatilized liquid material, the volume and/or velocity of air passing into the mouthpiece controlling a droplet size distribution of an aerosol delivered by the aerosol generator.

2. An aerosol generator as recited in claim 1, wherein the flow passage extends in a linear or non-linear direction, the flow passage being a capillary sized passage having a cross-sectional area of $8 \times 10^{-5}$ mm$^2$ to 80 mm$^2$.

3. An aerosol generator as recited in claim 1, wherein the flow passage is located in a monolithic or multilayer body of an electrically insulating material and/or the flow passage has a uniform cross section along the length thereof.

4. An aerosol generator as recited in claim 1, wherein the flow passage is located in a hand-held inhaler, the flow passage being a capillary sized passage having a maximum width of 0.1 to 0.5 mm, the outlet of the flow passage directing volatilized liquid material into the mouthpiece of the inhaler such that an aerosol is formed in the mouthpiece.

5. An aerosol generator as recited in claim 4, wherein the mouthpiece includes a mouthpiece opening through which aerosol is delivered to a patient, the outlet end of the flow passage being separated from the mouthpiece opening by a predetermined distance.

6. An aerosol generator as recited in claim 1, wherein an airflow entrainment control member forms the mouthpiece.

7. An aerosol generator as recited in claim 1, wherein the housing includes an outer wall enclosing the airflow entrainment control member, the outer wall including:

at least one vent hole which delivers ambient air to a space, the airflow entrainment control member separating the space from the interior of the mouthpiece, and the at least one air passageway extending through the airflow entrainment control member so as to provide airflow communication between the space and the interior of the mouthpiece.

8. An aerosol generator as recited in claim 4, wherein the interior of the mouthpiece has a volumetric capacity in a range between 5 cc and 10 cc.

9. An aerosol generator as recited in claim 7, wherein the airflow entrainment control member comprises a circular disc and the at least one air passageway comprises a plurality of air passageways.

10. An aerosol generator as recited in claim 1, wherein the at least one air passageway comprises a plurality of air passageways which permit ambient air to flow into the mouthpiece at a predetermined volume and/or velocity.

11. An aerosol generator as recited in claim 9, wherein the plurality of air passageways are circumferentially spaced apart.

12. An aerosol generator as recited in claim 1, wherein the at least one air passageway provides a volume and/or velocity of air effective to produce a mass median aerodynamic diameter of the aerosol produced by the aerosol generator in a range between 0.2 microns and 1 micron.

13. An aerosol generator as recited in claim 1, wherein the at least one air passageway provides a volume and/or velocity of air effective to produce a mass median aerodynamic diameter of the aerosol produced by the aerosol generator in a range between 1 micron and 2 microns.

14. An aerosol generator as recited in claim 1, the aerosol generator further comprising:

a power supply arranged to supply electrical current to the heater where the supplied electrical current resistively heats the heater and volatilizes the liquid material in the flow passage.

15. An aerosol generator as recited in claim 14, the aerosol generator further comprising:
a controller operably connected to the power supply, the controller allowing intermittent activation of the heater.

16. A method for generating an aerosol with the aerosol generator of claim 1, the method comprising:
supplying liquid material to the flow passage;
heating the flow passage so as to volatilize the liquid material in the flow passage;
directing the volatilized liquid material out of the flow passage into the mouthpiece located at the outlet end of the flow passage; and
forming an aerosol within the mouthpiece.

17. A method for generating an aerosol as recited in claim 16, wherein the liquid material comprises a medicated solution.

18. A method for generating an aerosol as recited in claim 16, the method further comprising controlling a volume and/or velocity of ambient air admixed with the vaporized liquid material within the mouthpiece by passing the ambient air through at least one air passageway of the airflow entrainment control member.

19. A method for generating an aerosol as recited in claim 18, wherein the airflow entrainment control member is replaceable, the method further comprising replacing the airflow entrainment control member with a different airflow entrainment control member effective to provide a desired aerosol size distribution.

20. A method for generating an aerosol as recited in claim 16, wherein the aerosol has a mass median aerodynamic diameter in a range between 0.2 microns and 1 micron.

21. A method for generating an aerosol as recited in claim 16, wherein the aerosol has a mass median aerodynamic diameter in a range between 1 micron and 2 microns.

22. An aerosol generator, comprising:
a housing having a flow passage therein;
a heater arranged along the flow passage and operable to vaporize liquid material passing through the flow passage;
a condensation region in fluid communication with an outlet end of the flow passage;
a source of liquid material to be volatilized, the source of liquid material being in fluid communication with an inlet of the flow passage; and
an airflow entrainment control member having a funnel shape and arranged such that a narrow end of the airflow entrainment member is disposed proximate the outlet end of the flow passage, the airflow entrainment control member admitting air to the condensation region and delivering a predetermined volume of air into the condensation region which mixes with the volatilized liquid material, the volume of air passing into the condensation region controlling a droplet size distribution of an aerosol delivered by the aerosol generator.

23. An aerosol generator as recited in claim 22, wherein a cone angle of the airflow entrainment control member is such that the mass median aerodynamic diameter of the aerosol produced by the aerosol generator is in a range between 0.2 microns and 1 micron.

24. An aerosol generator as recited in claim 22, wherein a cone angle of the airflow entrainment control member is such that the mass median aerodynamic diameter of the aerosol produced by the aerosol generator is in a range between 1 micron and 2 microns.

25. A method for generating an aerosol with an aerosol generator comprising:
a housing having a flow passage therein;
a heater arranged along the flow passage and operable to vaporize liquid material passing through the flow passage;
a mouthpiece having an interior thereof in fluid communication with an outlet end of the flow passage;
a source of liquid material to be volatilized, the source of liquid material being in fluid communication with an inlet of the flow passage; and
at least one air passageway which admits air from outside the mouthpiece to the interior of the mouthpiece, the at least one air passageway being operable to deliver a predetermined volume of air into the mouthpiece which mixes with the volatilized liquid material, the volume of air passing into the mouthpiece controlling a droplet size distribution of an aerosol delivered by the aerosol generator;
the method comprising:
supplying liquid material to the flow passage;
heating the flow passage to volatilize the liquid material in the flow passage;
directing the volatilized liquid material out of the flow passage into the mouthpiece located at the outlet end of the flow passage;
controlling a volume of ambient air admixed with the vaporized liquid material within the mouthpiece by passing the ambient air through a wide open end of a funnel-shaped airflow entrainment control member; and
forming an aerosol within the mouthpiece.

26. A method for generating an aerosol as recited in claim 25, wherein a narrow end of the airflow entrainment control member is located proximate the outlet end of the flow passage.

27. An aerosol generator, comprising:
a flow passage having an inlet and an outlet;
a heater arranged along the flow passage and operable to vaporize liquid material passing through the flow passage;
a source of the liquid material in fluid communication with the inlet of the flow passage;
a condensation region in fluid communication with the outlet of the flow passage; and
an airflow entrainment control member having an inlet end, an outlet end which is wider than the inlet end, the inlet end being disposed proximate the outlet of the flow passage, the airflow entrainment control member delivering a predetermined volume of air into the condensation region where the air mixes with the volatilized liquid material, the volume of air delivered into the condensation region controlling a droplet size distribution of an aerosol delivered by the aerosol generator.

28. An aerosol generator, comprising:
a housing having a flow passage therein;
a heater arranged along the flow passage and operable to vaporize liquid material passing through the flow passage;
a mouthpiece having an interior thereof in fluid communication with an outlet end of the flow passage;
a source of liquid material to be volatilized, the source of liquid material being in fluid communication with an inlet of the flow passage; and an airflow entrainment control member mounted at the outlet end of the flow passage, the airflow entrainment control member being adapted to admit air from outside the mouthpiece to the interior of the mouthpiece in a predetermined volume and/or velocity to mix with the volatilized liquid material so as to control a droplet size distribution of an aerosol delivered by the aerosol generator.

29. An aerosol generator, comprising:

a housing having a flow passage therein;

a heater arranged along the flow passage and operable to vaporize liquid material passing through the flow passage;

a condensation region in fluid communication with an outlet end of the flow passage;

a source of liquid material to be volatilized, the source of liquid material being in fluid communication with an inlet of the flow passage; and an airflow entrainment control member mounted at the outlet end of the flow passage, the airflow entrainment control member having a passageway through which air is admitted to the condensation region to mix with the volatilized liquid material so as to control a droplet size distribution of an aerosol delivered by the aerosol generator.

* * * * *

UNITED STATES PATENT AND TRADEMARK OFFICE
CERTIFICATE OF CORRECTION

PATENT NO. : 6,701,922 B1
APPLICATION NO. : 10/022739
DATED : March 9, 2004
INVENTOR(S) : Michael Hindle et al.

It is certified that error appears in the above-identified patent and that said Letters Patent is hereby corrected as shown below:

Column 7, line 54: "condensation regions 132 may" should read --condensation regions may--;

Claim 27, column 12, lines 53-57: "volatilized liquid material, the volume of air delivered into the condensation region controlling a droplet size distribution of an aerosol generator." should read --volatilized liquid material to form an aerosol, the volume of air delivered into the condensation region controlling a droplet size distribution of the aerosol deliveried by the aerosol generator.--;

Claim 28, column 13, lines 6-8: "volatilized liquid material so as to control a droplet size distribution of an aerosol delivered by the aerosol generator." should read --volatilized liquid material to form an aerosol so as to control a droplet size distribution of the aerosol delivered by the aerosol generator.--; and Claim 29, column 14, lines 10-12: "the volatilized liquid material so as to control a droplet size distribution of an aerosol delivered by the aerosol generator." should read --the volatilized liquid material to form an aerosol so as to control a droplet size distribution of the aerosol delivered by the aerosol generator.--.

Signed and Sealed this

Third Day of October, 2006

JON W. DUDAS
*Director of the United States Patent and Trademark Office*